*(12)* United States Patent
Chen et al.

US011340177B2

(10) Patent No.: US 11,340,177 B2
(45) Date of Patent: May 24, 2022

(54) CALIBRATION ASSEMBLY AND METHOD FOR CALIBRATING GEOMETRIC PARAMETERS OF CT APPARATUS

(71) Applicants: Nuctech Company Limited, Beijing (CN); Tsinghua University, Beijing (CN)

(72) Inventors: Zhiqiang Chen, Beijing (CN); Li Zhang, Beijing (CN); Zhenhua Zhao, Beijing (CN); Yunda Sun, Beijing (CN); Xin Jin, Beijing (CN); Wuyang Liang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 15/733,630

(22) PCT Filed: Jan. 20, 2020

(86) PCT No.: PCT/CN2020/073219
§ 371 (c)(1),
(2) Date: Sep. 21, 2020

(87) PCT Pub. No.: WO2020/192265
PCT Pub. Date: Oct. 1, 2020

(65) Prior Publication Data
US 2021/0223188 A1    Jul. 22, 2021

(30) Foreign Application Priority Data

Mar. 25, 2019 (CN) .......................... 201910226555.0

(51) Int. Cl.
*G01N 23/00* (2006.01)
*G01D 18/00* (2006.01)
(Continued)

(52) U.S. Cl.
CPC .......... *G01N 23/046* (2013.01); *A61B 6/032* (2013.01); *A61B 6/585* (2013.01); *G01V 5/005* (2013.01); *G01V 13/00* (2013.01)

(58) Field of Classification Search
CPC ......... A61B 6/032; A61B 6/583; A61B 6/585; A61B 6/027; A61B 6/541; A61B 6/5288;
(Continued)

(56) References Cited

U.S. PATENT DOCUMENTS 5,235,528 A * 8/1993 Silver .................. G06T 5/006
250/363.09
5,872,829 A * 2/1999 Wischmann ......... G01N 23/046
378/164

(Continued)

FOREIGN PATENT DOCUMENTS

CN      102743184 A    10/2012
CN      102750697 A    10/2012
(Continued)

OTHER PUBLICATIONS

"International Application Serial No. PCT/CN2020/073219, International Search Report dated Apr. 24, 2020", (Apr. 24, 2020), 5 pgs.
(Continued)

*Primary Examiner* — Irakli Kiknadze
(74) *Attorney, Agent, or Firm* — Schwegman Lundberg & Woessner, P.A.

(57) ABSTRACT

Disclosed are calibration assembly and calibration method of calibrating geometric parameters of a CT apparatus. The calibration assembly includes at least one calibration unit each including a plurality of calibration wires, and the plurality of calibration wires are arranged regularly in a same plane. The calibration assembly is easy to be processed
(Continued)

and can be used to calibrate geometric parameters of a CT apparatus, and the calibration operations are simple and easy to be implemented.

15 Claims, 4 Drawing Sheets

(51) Int. Cl.
| | |
|---|---|
| *G01N 23/046* | (2018.01) |
| *A61B 6/03* | (2006.01) |
| *A61B 6/00* | (2006.01) |
| *G01V 5/00* | (2006.01) |
| *G01V 13/00* | (2006.01) |

(58) Field of Classification Search
CPC ......... A61B 6/584; A61B 6/12; A61B 6/4071; A61B 6/4441; A61B 6/547; A61B 6/587; A61B 2560/0223; A61B 5/0215; A61B 5/026; A61B 5/055; A61B 5/318; A61B 5/6851; A61B 6/025; A61B 34/20; A61B 2034/2055; A61B 2034/105; A61B 34/10; A61B 2017/00725; A61B 2034/2048; A61B 6/037; A61B 6/4258; A61B 2090/378; A61B 2034/2068; A61B 2090/376; A61B 17/1757; A61B 6/504; A61B 8/12; A61B 18/1492; A61B 2017/00039; A61B 2018/00125; A61B 2018/00839; A61B 2034/2051; A61B 2090/365; A61B 5/415; A61B 5/418; A61B 6/507; A61B 5/4076; A61B 5/417; A61B 5/06; A61B 5/416; A61B 5/7285; A61B 6/425; A61B 6/4291; A61B 6/488; A61B 6/501; A61B 6/502; A61B 6/5258; A61B 6/482; A61B 6/5217; A61B 6/5205; A61B 6/4014; G01N 23/046; G01N 15/0826; G01N 15/088; G01N 2015/0846; G01N 2223/3035; G01N 27/327; G01N 2223/419; G01N 2223/612; G01N 23/044; G01N 23/083; G01T 7/005; G01T 1/161; G01T 1/1642; G01T 1/2985; G01T 1/1603; G01T 1/1615; G01T 1/02; G01T 1/1648; G01T 1/2018; G01T 1/1611; G01T 1/1644; G01T 1/1647; G01T 1/202; G01T 1/208; G01T 1/2907; G01T 7/00; G01T 7/10; G01T 7/12; G01V 13/00; G01V 5/005; G06T 7/00; G06T 2207/10081; G06T 2207/20008; G06T 2207/20056; G06T 2207/20192; G06T 2207/30101; G06T 5/002; G06T 5/003; G06T 5/10; G06T 5/20; G06T 2207/30204; G06T 7/60; G06T 7/73; G06T 7/80; G06T 2207/10116; G06T 7/0012; G06T 11/005; G06T 2207/30004; G06T 2207/30104; G06T 7/85; G06T 11/006; G06T 17/00; G06T 2207/10016; G06T 7/0008; G06T 11/008; G06T 5/001; G06T 5/50; G06T 7/337; G06T 2207/10104; G06K 9/40; G16H 30/40; G16H 40/40; G16H 40/67; A61N 2005/1061; A61N 5/1049; A61N 2005/1059; A61N 2005/1076; A61N 5/1075; A61N 1/0563; A61N 1/36071; A61N 1/36103; A61N 1/36507; H02J 50/15; H02J 50/20; H02J 50/90; H05G 1/26; G01B 15/045; G01B 15/025; G06N 3/084; G06N 20/00; G06N 3/0454
USPC .................................................. 378/4, 207, 8
See application file for complete search history.

(56) References Cited

U.S. PATENT DOCUMENTS

| | | | |
|---|---|---|---|
| 6,379,043 B1* | 4/2002 | Zylka | A61B 6/547 |
| | | | 378/207 |
| 7,950,849 B2 | 5/2011 | Claus et al. | |
| 8,007,173 B2 | 8/2011 | Paidi et al. | |
| 2007/0122020 A1 | 5/2007 | Claus et al. | |
| 2011/0085645 A1 | 4/2011 | Paidi et al. | |
| 2015/0093042 A1 | 4/2015 | Zhu et al. | |
| 2015/0216498 A1* | 8/2015 | Schulze | A61B 6/583 |
| | | | 378/207 |
| 2018/0144511 A1* | 5/2018 | Lee | G06T 7/337 |
| 2019/0302285 A1* | 10/2019 | Sato | G01T 7/005 |

FOREIGN PATENT DOCUMENTS

| | | |
|---|---|---|
| CN | 102743184 B | 10/2013 |
| CN | 102750697 B | 8/2014 |
| CN | 104778694 A | 7/2015 |
| CN | 105997126 A | 10/2016 |
| CN | 107133989 A | 9/2017 |
| CN | 104778694 B | 11/2017 |
| CN | 108596967 A | 9/2018 |
| CN | 108663386 A | 10/2018 |
| CN | 108955559 A | 12/2018 |
| CN | 105997126 B | 4/2019 |
| CN | 108663386 B | 8/2019 |
| CN | 209514098 U | 10/2019 |
| EP | 3129771 A1 | 2/2017 |
| EP | 3129771 B1 | 9/2019 |
| FR | 3019651 A1 | 10/2015 |
| FR | 3019651 B1 | 5/2016 |
| JP | 2017510814 A | 4/2017 |
| WO | WO-2013182080 A1 | 12/2013 |
| WO | WO-2015155466 A1 | 10/2015 |

OTHER PUBLICATIONS

"International Application Serial No. PCT/CN2020/073219, Written Opinion dated Apr. 24, 2020", (Apr. 24, 2020), 5 pgs.

* cited by examiner

FIG. 6

CALIBRATION ASSEMBLY AND METHOD FOR CALIBRATING GEOMETRIC PARAMETERS OF CT APPARATUS

CROSS-REFERENCE TO RELATED APPLICATION

This application is a U.S. National Stage Filing under 35 U.S.C. § 371 from International Application No. PCT/CN2020/073219, filed on Jan. 20, 2020, and published as WO2020/192265 on Oct. 1, 2020, which claims the benefit of priority of China Patent Application No. 201910226555.0, filed on Mar. 25, 2019 in the China National Intellectual Property Administration; the benefit of priority of each of which is hereby claimed herein, and which applications and publication are hereby incorporated herein by reference in their entireties.

BACKGROUND

Field of the Disclosure

The present disclosure relates to the technical field of security inspection, and in particular to a calibration assembly for calibrating geometric parameters of a CT apparatus and a calibration method for calibrating the geometric parameters of the CT apparatus by using the calibration assembly.

Description of the Related Art

In recent years, X-ray computed tomography (CT) technology has been widely used in medical and security inspection fields. At present, most CT apparatuses use a spiral cone beam scanning mode, in which a single focal spot light source and an arc detector are mounted on a circular slip ring, and the slip ring rotates to collect projection data at different angles, and then a 3D CT image is reconstructed by an analytical method. This type of apparatus usually has only a single scanning plane, relative positions of a focal spot of an X-ray machine and the detector are fixed and there are few geometric parameters involved in the system. However, a geometric error of the apparatus will cause problems such as a structural distortion of the reconstructed image, numerical inaccuracy and ring artifacts. In addition to the spiral cone beam type CT apparatus, a static CT apparatus in which a distributed light source is used has also begun to be used in the field of security inspection. Static CT apparatus has single or multiple scanning plane(s), each scanning plane contains multiple light source focal spots, and the focal spots may be arranged in a straight line, arc and other shapes; a detector is formed by splicing a number of the detector arms together, and each single detector arm may be straight, folded or curved. Compared with the spiral cone beam type CT apparatus, the static CT apparatus having no slip ring comprises an X light source and a detector fixed in position, and the angular coverage of the ray is guaranteed by multi-plane scanning, and static CT apparatus has the advantages such as a fast scanning speed and a low noise. Due to the particularity of its scanning geometry, an iteration reconstruction method is usually used for the static CT apparatus to obtain a three-dimensional image. This method does not require that the geometric arrangement meets particular conditions, but the positions of the focal spot of the X-ray machine and the detector crystal need to be accurately positioned, and coordinate systems of different scanning planes also need to be unified. However, compared with a single target-point light source, the distributed light source has larger volume and weight, and the mechanical error of its installation will be correspondingly larger. Due to a wide distribution range of the focal spots of the light source, the geometric deviation of the light source as a whole usually causes the target-point position to deviate significantly from the design value, and offset distances and offset directions of respective focal spots may be different from each other, resulting in the deformation of the reconstructed object and an inaccurate reconstruction value, adversely affecting the spatial resolution and material identification of the apparatus. In addition, there will be errors in the installation of the detector arm, so it is necessary to perform geometric correction on the apparatus.

SUMMARY

The present disclosure is aimed to overcome or alleviate at least one aspect of the above-mentioned and other problems and disadvantages in the prior art.

According to an embodiment of an aspect of the present disclosure, there is provided a calibration assembly for calibrating geometric parameters of a CT apparatus, the calibration assembly comprising at least one calibration unit each including a plurality of calibration wires, the plurality of calibration wires being regularly arranged in a same plane.

In some embodiments, the calibration wire is in a shape of a straight line, a fold line or an arc.

In some embodiments, each calibration unit further comprises a fixing member configured to fix the plurality of calibration wires.

In some embodiments, the plurality of calibration wires are configured to be directly fixed on a conveyor belt of the CT apparatus or in a passage of the CT apparatus.

In some embodiments, the plurality of calibration wires of the calibration unit are arranged at equal intervals.

In some embodiments, the plurality of calibration wires are arranged to be parallel to or at an angle to a conveying direction of a conveyor belt of the CT apparatus.

In some embodiments, the at least one calibration unit includes a first calibration unit, and the plurality of calibration wires of the first calibration unit are arranged in a horizontal plane or vertical plane parallel to a conveying direction of a conveyor belt of the CT apparatus.

In some embodiments, the at least one calibration unit further includes a second calibration unit, and a plane in which the plurality of calibration wires of the second calibration unit are located is perpendicular to a plane in which the plurality of calibration wires of the first calibration unit are located.

In some embodiments, the at least one calibration unit further includes a third calibration unit, a plane in which the plurality of calibration wires of the third calibration unit is located is perpendicular to the plane in which the plurality of calibration wires of the first calibration unit are located, and the second calibration unit and the third calibration unit are located at opposite ends of the first calibration unit in a direction perpendicular to the conveying direction of the conveyor belt respectively.

In some embodiments, the calibration wire is cylindrical.

In some embodiments, the calibration wire has a diameter in a range of 0.5 mm to 5 mm.

According to an embodiment of another aspect of the present disclosure, there is provided a method for calibrating geometric parameters of a CT apparatus by using the calibration assembly described herein, the method comprising the following steps:

S1: calculating theoretical positions of centroids of the calibration wires according to geometric parameters of the calibration assembly;

S2: scanning the calibration assembly, and extracting, from a scanning plane, at least one set of sinograms including projections of the calibration wires;

S3: obtaining a position of the centroid of each of the calibration wires of the calibration assembly from the sinograms;

S4: establishing, for each of the calibration wires, by using an X-ray machine as a reference system based on an intersection point of a virtual connection line, between a focal spot and the centroid of the each of the calibration wires, with a detector, and based on the position of the centroid of the each of the calibration wires obtained in the step S3, an optimization model for parameters of the detector and the position of the centroids of the calibration wires, and solving the optimization model to obtain the positions of the centroids of all the calibration wires within the scanning plane;

S5: matching, by using a position matching algorithm, the position of the centroid of the each of the calibration wires obtained in the step S4 with the theoretical position calculated in the step S1, so as to correct the position of the centroid of the each of the calibration wires obtained in the step S4; and S6: establishing, based on the corrected position of the centroid of the each of the calibration wires, an optimization model for the parameters of the detector for all calibration wires, and solving the optimization model to obtain geometric parameters of the detector in the scanning plane.

In some embodiments, when there are multiple scanning planes, the step S2 comprises:

extracting, from each scanning plane, at least one set of sinograms containing the projection of the each of the calibration wires, such that the sinograms extracted from different scanning planes correspond to a same slicing position of the calibration assembly; and the method further comprises, after the step S6, the following steps of:

S7: repeating the steps S3 to S6 for respective scanning planes to obtain the geometric parameters of the detector and the positions of the centroid of the each of the calibration wires in the respective scanning planes; and S8: through the position matching algorithm, expressing the positions of the centroid of the each of the calibration wires obtained in the step S6 in a unified coordinate system, such that the positions of the centroid of the calibration wire in different scanning planes are the same, so as to obtain a position of the focal spot of the X-ray machine and a position of a crystal of the detector.

DETAILED DESCRIPTION OF THE EMBODIMENTS

Although the present disclosure will be fully described with reference to the drawings comprising preferred embodiments of the present invention, it should be understood before the description that those skilled in the art can modify the invention described herein while obtaining the technical effects of the present invention. It should be understood that the above description is a broad disclosure for those skilled in the art, and its content is not intended to limit the exemplary embodiments described in the present disclosure.

In the following detailed description, for purposes of explanation, numerous specific details are set forth in order to provide a thorough understanding of the disclosed embodiments. It will be apparent, however, that one or more embodiment(s) may be practiced without these specific details. In other instances, well-known structures and devices are schematically shown in order to simplify the drawings.

According to a general concept of the present disclosure, there is provided a calibration assembly for calibrating geometric parameters of a CT apparatus. The calibration assembly comprises at least one calibration unit each including a plurality of calibration wires, and the plurality of calibration wires are regularly arranged in a same plane.

Figure 1:
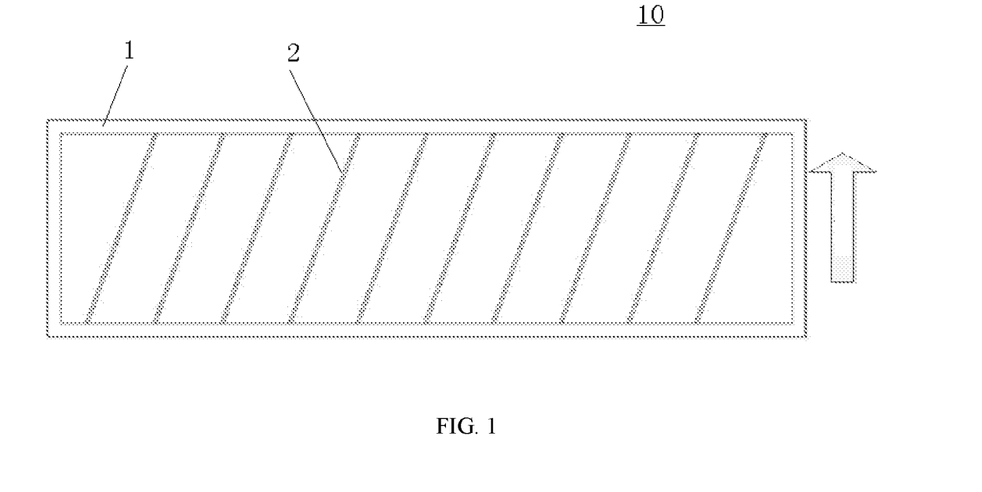
FIG. 1 is a schematic structural diagram of a calibration assembly for calibrating geometric parameters of a CT apparatus according to an exemplary embodiment of the present disclosure.

FIG. 1 is a schematic structural diagram of a calibration assembly for calibrating geometric parameters of a CT apparatus according to an exemplary embodiment of the present disclosure. As shown in FIG. 1, the calibration assembly for calibrating geometric parameters of a CT apparatus comprises a calibration unit 10, which comprises a plurality of calibration wires 2 and a fixing member 1. The plurality of calibration wires 2 are configured to be regularly arranged in a horizontal plane parallel to a conveying direction of a conveyor belt. The calibration wire 2 is usually made of a high-absorptivity material, such as metal. The calibration wire 2 can be flexible (such as steel wire, etc.) or rigid (such as steel rod, etc.). Each calibration wire 2 is in a straight shape, and the cross-sectional shape of the calibration wire 2 includes but is not limited to a cylindrical shape, and its diameter may be, for example, 0.5 mm to 5 mm. The fixing member 1 is configured to fix the plurality of calibration wires 2 so as to ensure positions of the calibration wires 2 are fixed such that the relative positions between the different calibration wires 2 are consistent with theoretical design values. The fixing member 1 may be made of a low-absorptivity material.

It should be noted that although the calibration wire shown in this embodiment has a straight shape, it will be understood by those skilled in the art that in some other embodiments of the present disclosure, the calibration wire 2 may also be in the shape of a fold line, an arc, or in other regular shapes. In addition, it will be understood by those skilled in the art that in some other embodiments of the present disclosure, the calibration wire 2 may also be configured to be directly fixed on the conveyor belt of the CT apparatus or in a passage of the CT apparatus.

As shown in FIG. 1, in this exemplary embodiment, the plurality of calibration wires 2 of the calibration unit 10 are parallel to each other and are arranged at equal intervals, for facilitating subsequent calculation. In addition, in this embodiment, the plurality of calibration wires 2 are configured to be at an angle to the conveying direction of the conveyor belt of the CT apparatus. However, it will be understood by those skilled in the art that in some other embodiments of the present disclosure, the plurality of calibration wires 2 of the calibration unit 10 may also be configured to be parallel to the conveying direction of the conveyor belt.

Figure 2:
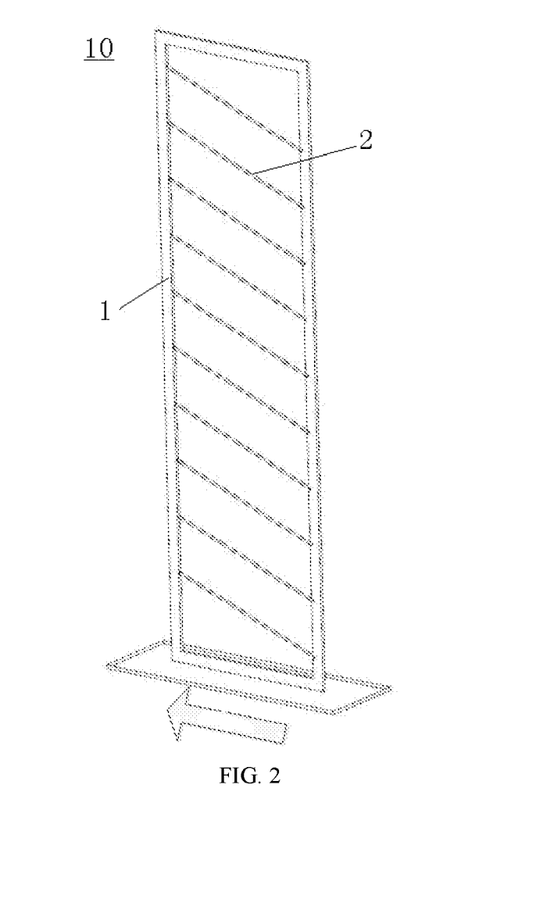
FIG. 2 is a schematic structural diagram of a calibration assembly for calibrating geometric parameters of a CT apparatus according to another exemplary embodiment of the present disclosure.

FIG. 2 is a schematic structural diagram of a calibration assembly for calibrating geometric parameters of a CT apparatus according to another exemplary embodiment of the present disclosure. As shown in FIG. 2, a plurality of calibration wires 2 of the calibration unit 10 are parallel to each other and are arranged at equal intervals in a vertical plane parallel to the conveying direction (as denoted by the arrow shown in FIG. 2) of the conveyor belt. The plurality of calibration wires 2 are at an angle to the conveying direction of the conveyor belt.

Figure 3:
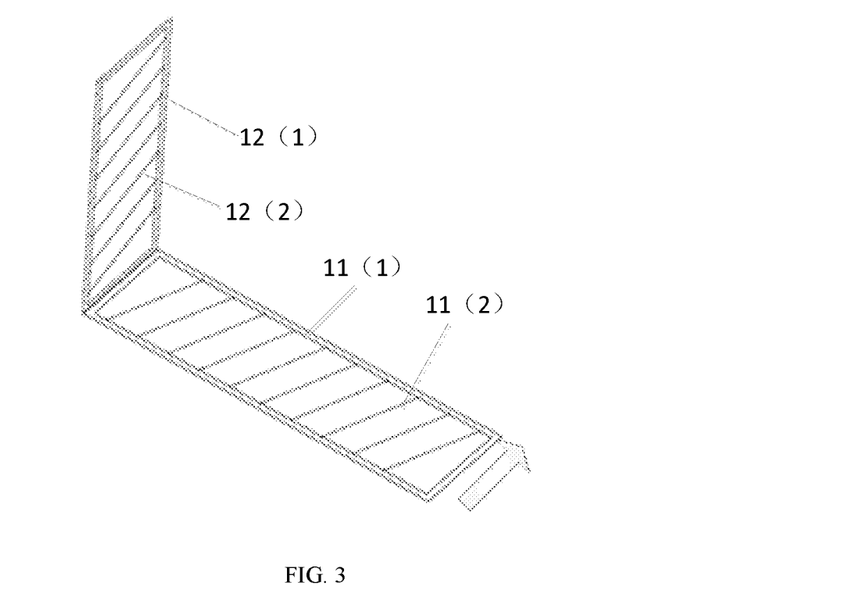
FIG. 3 is a schematic structural diagram of a calibration assembly for calibrating geometric parameters of a CT apparatus according to yet another exemplary embodiment of the present disclosure.

FIG. 3 is a schematic structural diagram of a calibration assembly for calibrating geometric parameters of a CT apparatus according to yet another exemplary embodiment of the present disclosure. As shown in FIG. 3, the calibration assembly comprises two calibration units including a first calibration unit 11 and a second calibration unit 12. In examples, the first calibration unit 11 and the second calibration unit 12 each include a plurality of calibration wires 2 and a fixing member 1, the plurality of calibration wires 2 are arranged regularly, and each calibration wire 2 is in a straight form. The fixing member 1 is configured to fix the plurality of calibration wires 2. The plurality of calibration wires 2 of the first calibration unit 11 are arranged at equal intervals in a horizontal plane parallel to the conveying direction (as denoted by the arrow shown in FIG. 3) of the conveyor belt of the CT apparatus. A plane in which the plurality of calibration wires 2 of the second calibration unit 12 are located is perpendicular to the plane in which the plurality of calibration wires 2 of the first calibration unit 11 are located, so that the entire calibration assembly is L-shaped.

Figure 4:
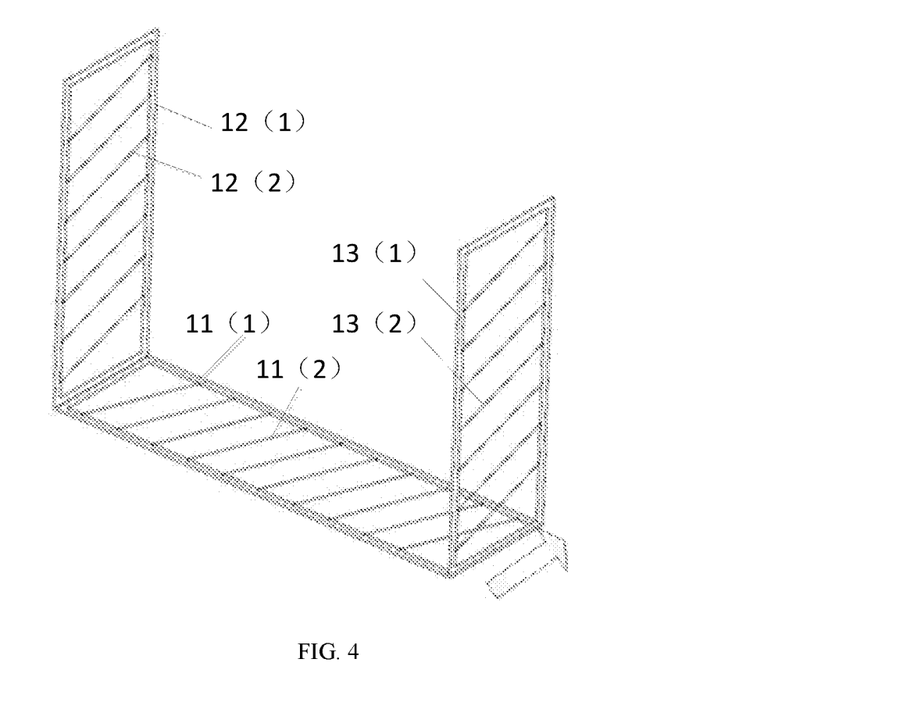
FIG. 4 is a schematic structural diagram of a calibration assembly for calibrating geometric parameters of a CT apparatus according to still another exemplary embodiment of the present disclosure.

FIG. 4 is a schematic structural diagram of a calibration assembly for calibrating geometric parameters of a CT apparatus according to still another exemplary embodiment of the present disclosure. As shown in FIG. 4, the calibration assembly comprises three calibration units including a first calibration unit 11, a second calibration unit 12 and a third calibration unit 13. In examples, the first calibration unit 11, the second calibration unit 12 and the third calibration unit 13 each comprise a plurality of calibration wires 2 and a fixing member 1, the plurality of calibration wires 2 are arranged regularly, and each calibration wire 2 is straight; the fixing member 1 is configured to fix the plurality of calibration wires 2. In examples, the plurality of calibration wires 2 of the first calibration unit 11 are arranged at equal intervals in a horizontal plane parallel to the conveying direction (as denoted by the arrow shown in FIG. 4) of the conveyor belt of the CT apparatus. A plane in which the plurality of calibration wires 2 of the second calibration unit 12 are located is perpendicular to a plane in which the plurality of calibration wires 2 of the first calibration unit 11 are located, a plane in which the plurality of calibration wires 2 of the third calibration unit 13 are located is perpendicular to the plane in which the plurality of calibration wires 2 of the first calibration unit 11 are located, and the second calibration unit 11 and the third calibration unit 13 are located at opposite ends of the first calibration unit 11 in a direction perpendicular to the conveying direction of the conveyor belt respectively, so that the entire calibration assembly is U-shaped.

Figure 5:
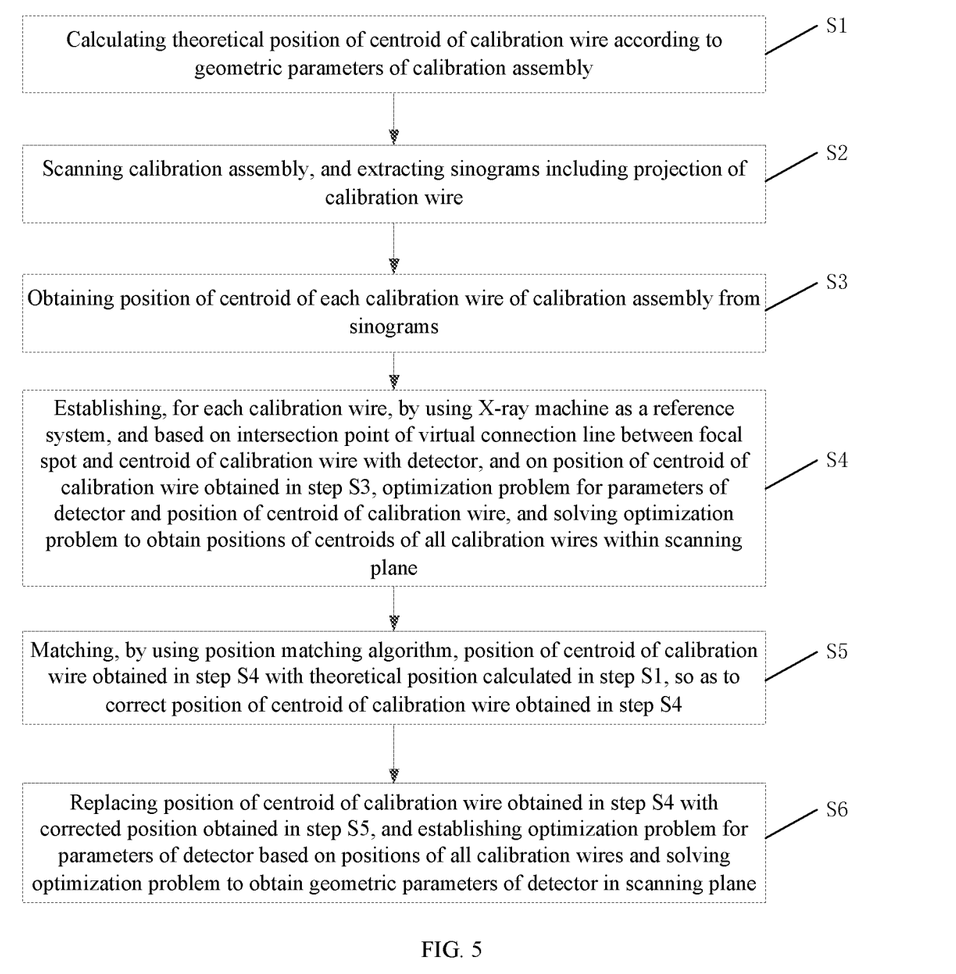
FIG. 5 is a flowchart of a calibration method for calibrating geometric parameters of a CT apparatus according to an exemplary embodiment of the present disclosure.

As shown in FIG. 5, the present disclosure also provides a calibration method for calibrating geometric parameters of a CT apparatus by using the abovementioned calibration assembly, and the method comprises the following steps of:

S1: calculating a theoretical position $\{\bar{x}_m\}$ of a centroid of the calibration wire 2 according to design parameters of the calibration assembly;

S2: scanning the calibration assembly, and extracting, from a scanning plane, sinograms containing a projection of the calibration wire; specifically, the calibration assembly is placed on the conveyor belt of the CT apparatus and is scanned while the conveyor belt runs at a low speed during the scanning process, and a starting position of the calibration assembly is detected to ensure that the projections obtained from different scanning planes correspond to the sinogram at a same position of the calibration assembly; in addition, three or more sinograms for example may be extracted at equal intervals from each scanning plane;

S3: obtaining a position of the centroid of the calibration wire 2 from each sinogram by using an image processing method; due to limitation on the size of a crystal of the detector, the detection accuracy of the position of the centroid of the calibration wire 2 is half of the width of the crystal; it is assumed that the calibration assembly comprises N calibration wires 2, a total of M sets of sinograms were collected; due to movement of the conveyor belt, the positions of the centroids of the calibration wires 2 on respective sinograms are different from one another, so M*N sets of projection data of the calibration wires are collected from each scanning plane; if a beam is emitted from a focal spot k, the crystal reference number of the true projection of the centroid of the calibration wire m onto the plane of the detector is expressed as $\hat{b}_{k,m}$;

S4: establishing, for each single calibration wire in the scanning plane, by using the X-ray machine as a reference system, and based on an intersection point of a virtual connection line between a focal spot and the centroid of the calibration wire m with the detector, and on the position of the centroid of the calibration wire m obtained in the step S3, an optimization model for parameters of the detector and the position of the centroid of the calibration wire, and solving the optimization model to obtain the positions of the centroids of all the calibration wires within the scanning plane; the geometric parameters of the detector are related to the arrangement of the crystal of the detector; for example, geometric parameters of a straight-line shaped detector are determined by a starting position of the detector and an arrangement direction of the crystals, and geometric parameters of an arc detector are determined by a center and a radius of a circle, and starting angle of the detector; taking the straight-line shaped detector as an example, the parameters of the detector are expressed as (y,d), where y is the starting position of the detector, and d is a direction vector of the arrangement of the crystals of the detector; a straight line equation for the detector is expressed as L(y,d), the size of the crystal size is expressed as δ; the position of the calibration wire m is expressed as $x_m$, and the position of the focal spot k is expressed as $z_k$; a virtual connection line between the calibration wire and the focal spot is expressed as $L(x_m,z_k)$; the two straight lines $L(y,d)$ and $L(x_m,z_k)$ intersect at a position $p_{k,m}$, corresponding to a position $b_{k,m}=(p_{k,m}-y)/\delta$ on the crystal; according to the step S3, the projections of the focal spot k and the calibration wire m onto the plane of the detector have an actual position $\hat{b}_{k,m}$ in aspect of the crystal reference number; the parameters (y,d) and $x_m$ are optimized by minimizing $|b_{k,m}-\hat{b}_{k,m}|$; the above process can be described or expressed as the following optimization model:

$$\min_{y,d,x_m} \sum_k \left\| \frac{f(L(y,d), L(x_m, z_k)) - y}{\delta} - \hat{b}_{k,m} \right\|_p,$$

where $f(\bullet,\bullet)$ represents coordinates of the intersection point of the two straight lines and $\|\bullet\|_p$ represents the p-norm. For each calibration wire, the above optimization model is solved to obtain the positions $\{\tilde{x}_m\}$ of all calibration wires. Simulated annealing method can be used to solve the above optimization model;

S5: matching, by using a position matching algorithm, the position of the centroid of the calibration wire m obtained in the step S4 with the theoretical position calculated in the step S1, so as to correct the position of the centroid of the calibration wire m obtained in the step S4; since there is an error in each of the steps S3 and S4, and the placement posture of the calibration assembly is uncertain, there will be a difference of the position $\{\tilde{x}_m\}$ of the centroid of the calibration wire m obtained in the step S4 from the theoretical position $\{\overline{x}_m\}$ calculated in the step S1; the position $\{\tilde{x}_m\}$ is calibrated by matching and registering, through a position matching algorithm, the position of the centroid of the calibration wire calculated in the step S4 with the theoretical position $\{\overline{x}_m\}$ calculated in the step S1, so as to obtain the final position $\{\hat{x}_m\}$ of the calibration wire m;

S6: replacing the position of the centroid of the calibration wire m obtained in the step S4 with the corrected position obtained in the step S5, and establishing an optimization model for parameters of the detector based on the positions of all the calibration wires and solving the optimization model so as to obtain geometric parameters of the detector in the scanning plane. For example, according to the intersection relationship, the following optimization model is established:

$$\min_{y,d} \sum_{m,k} \left\| \frac{f(L(y,d), L(\hat{x}_m, z_k)) - y}{\delta} - \hat{b}_{k,m} \right\|_p.$$

The geometric parameters y and d of the detector can be obtained by solving the above optimization model.

Figure 6:
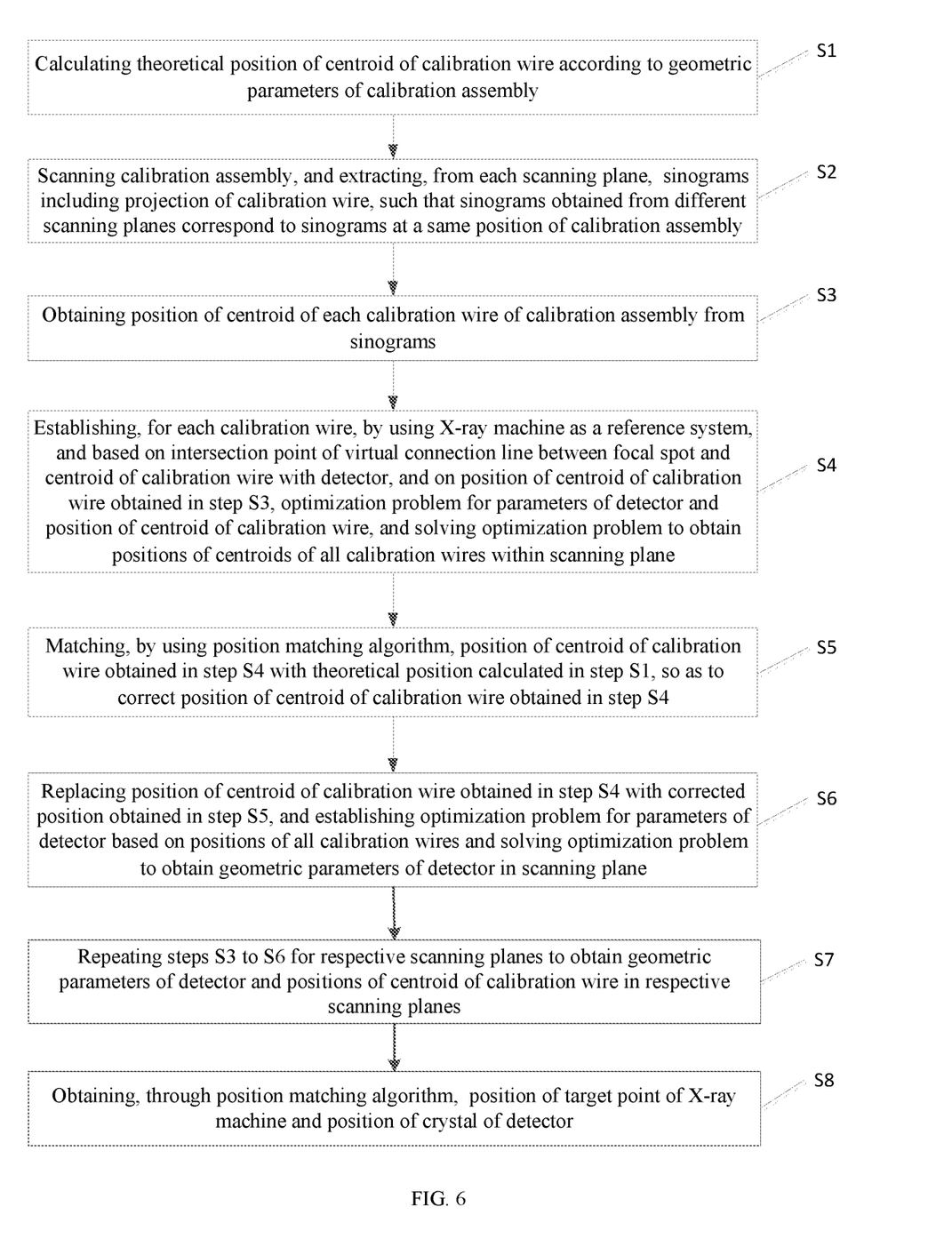
FIG. 6 is another flowchart of a calibration method for calibrating geometric parameters of a CT apparatus according to an exemplary embodiment of the present disclosure.

As shown in FIG. 6, in an example of the present disclosure, when there are a plurality of scanning planes, the step S2 comprises extracting, from each scanning plane, at least one set of sinograms containing the projection of the calibration wire, such that the sinograms extracted from different scanning planes correspond to a same slicing position of the calibration assembly; and a starting position of the calibration assembly may be detected to ensure that the projections obtained from different scanning planes correspond to the sinogram at a same position of the calibration assembly; in addition, three or more sinograms for example may be extracted at equal intervals from each scanning plane. The method further comprises, after the step S6, the following steps of:

S7: repeating the steps S3 to S6 for respective scanning planes to obtain the geometric parameters of the detector and the positions of the centroid of the calibration wire in the respective scanning planes; and S8: through a position matching algorithm, expressing the positions of the centroid of the calibration wire 2 obtained in the step S6 in a unified coordinate system, such that the positions of the centroid of the calibration wire 2 in different scanning planes are the same, so as to obtain a position of the focal spot of the X-ray machine and a position of the crystal of the detector. Taking the conveying direction of the conveyor belt as the direction of the z coordinate axis, since the position of the calibration assembly remains stationary relative to the moving conveyor belt, the position of the calibration wire is constant in the x-y plane among different planes. Through the position matching algorithm, the positions of the calibration wire obtained in the step S6 are expressed in a unified coordinate system, so that the positions of the calibration wire obtained in different planes are consistent with each other, and correspondingly the position of the focal spot of the X-ray machine and the position of the crystal of the detector can be obtained.

According to the calibration assembly and calibration method of calibrating geometric parameters of a CT apparatus described in above embodiments of the present disclosure, the calibration assembly comprises at least one calibration unit each including a plurality of calibration wires, and the plurality of calibration wires are arranged at preset intervals in a plane perpendicular to the conveying direction of the conveyor belt of the CT apparatus, and each calibration wire is in the shape of a straight line or other preset shapes. When in use, the calibration assembly is placed on the conveyor belt or in the passage of the CT apparatus so as to be scanned, and the relative positions of the X-ray machine and the detector are calibrated based on the projection position of the calibration wire onto the plane of the detector, and the position of the calibration wire is obtained, so as to obtain the position of the focal spot of the X-ray machine and the position of the crystal of the detector. The calibration assembly and calibration method of calibrating geometric parameters of a CT apparatus is easy to be processed and can be applied to an area array detector and a linear array detector, and can be used to calibrate geometric parameters of a spiral cone beam type CT apparatus and a static CT apparatus.

It will be understood by those skilled in the art that the embodiments described above are exemplary, and may be improved by those skilled in the art. The structures described in the various embodiments can be combined freely without conflicting in structure or principle.

After describing the exemplary embodiments of the present invention in detail, it will be clearly understood by those skilled in the art that various changes and modifications can be made without departing from the scope and spirit of the appended claims, and the present invention is not limited to the implementations of the exemplary embodiments described in the description.

What is claimed is:

1. A method for calibrating geometric parameters of a CT apparatus by using a calibration assembly, the calibration assembly comprising at least one calibration unit each comprising a plurality of calibration wires, the plurality of calibration wires being regularly arranged in a same plane, the method comprising steps of:

S1: calculating theoretical positions of centroids of the calibration wires according to geometric parameters of the calibration assembly;

S2: scanning the calibration assembly, and extracting, from a scanning plane, at least one set of sinograms including projections of the calibration wires;

S3: obtaining a position of the centroid of each of the calibration wires of the calibration assembly from the sinograms;

S4: establishing, for each of the calibration wires, by using an X-ray machine as a reference system based on an intersection point of a virtual connection line, between a focal spot and the centroid of the each of the calibration wires, with a detector, and based on the position of the centroid of the each of the calibration wires obtained in the step S3, an optimization model for parameters of the detector and the position of the centroids of the calibration wires, and solving the optimization model to obtain the positions of the centroids of all the calibration wires within the scanning plane;

S5: matching, by using a position matching algorithm, the position of the centroid of the each of the calibration wires obtained in the step S4 with the theoretical position calculated in the step S1, so as to correct the position of the centroid of the each of the calibration wires obtained in the step S4; and S6: establishing, based on the corrected position of the centroid of the each of the calibration wires, an optimization model for the parameters of the detector for all calibration wires, and solving the optimization model to obtain geometric parameters of the detector in the scanning plane.

2. The method according to claim 1, wherein, in a case where multiple scanning planes are included, the step S2 comprises:

extracting, from each scanning plane, at least one set of sinograms containing the projection of the each of the calibration wires, such that the sinograms extracted from different scanning planes correspond to a same slicing position of the calibration assembly; and the method further comprises, after the step S6, the following steps of:

S7: repeating the steps S3 to S6 for respective scanning planes to obtain the geometric parameters of the detector and the positions of the centroid of the each of the calibration wires in the respective scanning planes; and S8: through the position matching algorithm, expressing the positions of the centroid of the each of the calibration wires obtained in the step S6 in a unified coordinate system, such that the positions of the centroid of the calibration wire in different scanning planes are the same, so as to obtain a position of the focal spot of the X-ray machine and a position of a crystal of the detector.

3. The method according to claim 1, wherein the at least one calibration unit includes a first calibration unit, and the plurality of calibration wires of the first calibration unit are provided to be arranged in a horizontal plane or vertical plane parallel to a conveying direction of a conveyor belt of the CT apparatus.

4. The method according to claim 3, wherein the at least one calibration unit further includes a second calibration unit, and a plane in which the plurality of calibration wires of the second calibration unit are located is perpendicular to a plane in which the plurality of calibration wires of the first calibration unit are located.

5. The method according to claim 4, wherein the at least one calibration unit further includes a third calibration unit, a plane in which the plurality of calibration wires of the third calibration unit is located is perpendicular to the plane in which the plurality of calibration wires of the first calibration unit are located, and the second calibration unit and the third calibration unit are located at opposite ends of the first calibration unit in a direction perpendicular to the conveying direction of the conveyor belt respectively.

6. The method according to claim 1, wherein the calibration wire is in a shape of a straight line, a fold line or an arc.

7. The method according to claim 1, wherein each calibration unit further comprises a fixing member configured to fix the plurality of calibration wires.

8. The method according to claim 1, wherein the plurality of calibration wires are provided to be directly fixed on a conveyor belt of the CT apparatus or in a passage of the CT apparatus.

9. The method according to claim 1, wherein the plurality of calibration wires of the calibration unit are arranged at equal intervals.

10. The method according to claim 9, wherein the plurality of calibration wires are arranged to be parallel to or at an angle to a conveying direction of a conveyor belt of the CT apparatus.

11. The method according to claim 9, wherein the at least one calibration unit comprises a first calibration unit, and the plurality of calibration wires of the first calibration unit are provided to be arranged in a horizontal plane or vertical plane parallel to a conveying direction of a conveyor belt of the CT apparatus.

12. The method according to claim 11, wherein the at least one calibration unit further comprises a second calibration unit, and a plane in which the plurality of calibration wires of the second calibration unit are located is perpendicular to a plane in which the plurality of calibration wires of the first calibration unit are located.

13. The method according to claim 12, wherein the at least one calibration unit further comprises a third calibration unit, a plane in which the plurality of calibration wires of the third calibration unit are located is perpendicular to the plane in which the plurality of calibration wires of the first calibration unit are located, and the second calibration unit and the third calibration unit are located at opposite ends of the first calibration unit in a direction perpendicular to the conveying direction of the conveyor belt respectively.

14. The method according to claim 1, wherein the calibration wire is cylindrical.

15. The method according to claim 14, wherein the calibration wire has a diameter in a range of 0.5 mm to 5 mm.

\* \* \* \* \*